United States Patent [19]

Bagchi et al.

[11] Patent Number: 5,716,642

[45] Date of Patent: Feb. 10, 1998

[54] MICROPRECIPITATION OF NANOPARTICULATE PHARMACEUTICAL AGENTS USING SURFACE ACTIVE MATERIAL DERIVED FROM SIMILAR PHARMACEUTICAL AGENTS

[75] Inventors: Pranab Bagchi, Webster, N.Y.; Gregory L. McIntire, West Chester, Pa.; John R. Minter, Rochester, N.Y.

[73] Assignee: Nano Systems L.L.C., Collegeville, Pa.

[21] Appl. No.: 370,928

[22] Filed: Jan. 10, 1995

[51] Int. Cl.$^6$ ..................................................... A61K 9/14
[52] U.S. Cl. ........................... 424/489; 424/490; 424/9.1; 424/9.4
[58] Field of Search ........................... 424/489, 7.1, 404, 424/9

[56] References Cited

U.S. PATENT DOCUMENTS

| | | | |
|---|---|---|---|
| 4,107,288 | 8/1978 | Oppenheim et al. | 424/22 |
| 4,250,113 | 2/1981 | Nordal et al. | 564/153 |
| 4,310,507 | 1/1982 | Luckey | 424/4 |
| 4,396,598 | 8/1983 | Lin | 424/5 |
| 4,489,055 | 12/1984 | Couvreur et al. | 424/7.1 |
| 4,540,602 | 9/1985 | Motoyama et al. | 427/213.31 |
| 4,713,249 | 12/1987 | Schroder | 424/488 |
| 4,725,442 | 2/1988 | Haynes | 424/490 |
| 4,826,689 | 5/1989 | Violanto et al. | 424/489 |
| 5,118,528 | 6/1992 | Fessi et al. | 427/213.36 |
| 5,145,684 | 9/1992 | Liversidge et al. | 424/489 |
| 5,260,478 | 11/1993 | Bacon et al. | 560/110 |
| 5,264,610 | 11/1993 | Bacon | 560/47 |
| 5,314,679 | 5/1994 | Lewis et al. | 424/9 |
| 5,318,767 | 6/1994 | Liversidge et al. | 424/4 |

OTHER PUBLICATIONS

Radiology, Jan. 1982, vol. 142, pp. 115–118.

Lachman, et al, "The Theory and Practice of Industrial Pharmacy", Chapter 2, Milling, p. 45, (1986).

Handbook of Experimental Pharmacology, vol. 73, pp. 56–73, 1984.

Investigative Radiology, vol. 29, Jul.–Aug. 1994.

International Journal of Pharmaceutics, 52(1989) 101–108.

*Primary Examiner*—Thurman K. Page
*Assistant Examiner*—William E. Benston, Jr.
*Attorney, Agent, or Firm*—Rudman & Balogh

[57] ABSTRACT

This invention describes the preparation of nanoparticulate pharmaceutical agent dispersion via a process that comprises the dissolution of the said pharmaceutical agent in an alkaline solution and then neutralizing the said solution with an acid in the presence of suitable surface-modifying, surface-active agents to form a fine particle dispersion of the said pharmaceutical agent. A combination of surface active surface modifying agents comprising a nonionic surface active substance and an anionic surface active material having a chemical structure which is at least on a molecular basis 75% similar to the pharmaceutical agent is used. This process is preferably followed by steps of diafiltration clean-up of the dispersion and then concentration of it to a desired level. This process of dispersion preparation leads to microcrystalline particles of Z-average diameters smaller than 400 nm as measured by photon correlation spectroscopy. Various modifications of precipitation schemes are described, many of which are suitable for large-scale manufacture of these agent dispersions.

30 Claims, 9 Drawing Sheets

STEP 1: PHARMACEUTICAL AGENT + AQUEOUS BASE

STEP 2: AQUEOUS, ALKALINE AGENT SOLUTION + AQUEOUS SURFACTANT SOLUTION (SLIGHTLY BASIC)

STEP 3: AQUEOUS ALKALINE AGENT AND SURFACTANT SOLUTION + ACID SOLUTION

NANOPARTICULATE AGENT DISPERSION

STEP 4: DIALYSIS OR DIAFILTRATION

SALT-FREE NANOPARTICULATE AGENT DISPERSION

STEP 5: CONCENTRATION

SALT-FREE CONCENTRATED NANOPARTICULATE AGENT DISPERSION

(WITH T908 & Y)　　　(WITH T908 & Y)　　　(WITH F108 & Y)

MICROPRECIPITATION OF NANOPARTICULATE PHARMACEUTICAL AGENTS USING SURFACE ACTIVE MATERIAL DERIVED FROM SIMILAR PHARMACEUTICAL AGENTS

FIELD OF THE INVENTION

This invention deals with microprecipitation of pharmaceautical agents (diagnostic and therapeutic) as stable, colloidal, nanoparticulate dispersions for pharmaceutical use in the presence of at least a nonionic and at least an anionic surface active surface modifying agent whose chemical structure is at least 75% identical on a molecular basis to the pharmaceutical agent.

BACKGROUND OF INVENTION

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/mL, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lachman, et al., *The Theory and Practice of Industrial Pharmacy*, Chapter 2, "Milling," p. 45, (1986), the limit of fineness is reached in the region of 100 microns (100,000 nm) when material cakes on the milling chamber. Lachman, et al. note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 μm (1,000–50,000 nm).

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptable large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

U.S. Pat. No. 4,540,602 (Motoyama, et al.) discloses a solid drug pulverized in a aqueous solution of a water-soluble high molecular weight substance using a wet grinding machine. However, Motoyama, et al. teach that as a result of such wet grinding, the drug is formed into finely divided particles ranging from 0.5 μm (500 nm) or less to 5 μm (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance and results in the formation of non-crystalline nanoparticle. A somewhat more involved solvent shift method is described in U.S. Pat. No. 4,826,689 (Violanto) which produces uniform particles of drugs with diameters ranging between 0.5 to 1.0 μm. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmaceutically active material. However, the particles comprise a crosslinked matrix of macromolecules having the active material supported on or incorporated into the matrix.

U.S. Pat. No. 4,725,442 (Haynes) describes water insoluble drug materials solubilized in an organic liquid and incorporated in microencapsules of phospholipids. However, the toxic effects of solubilizing organic liquids is difficult to overcome. Other methods of formation of pharmaceutical drug microencapsule include:

a) Micronizing a slightly-soluble drug by subjecting a mixture of the drug and a sugar or sugar alcohol to high-speed stirring comminution or impact comminution (EP 411,629A) together with suitable excipients or diluents. Such a method of encapsule formation does not lead to particle size as small as obtained by milling.
b) Polymerization of a monomer in the presence of the active drug material and a surfactant can lead to small-particle microencapsule (International Journal of Pharmaceutics, Vol. 52, pp. 101–108, 1989). This process, however, contains difficult-to-remove contaminants such as toxic monomers. Complete removal of such monomers can be expensive in manufacturing scales.
c) Co-dispersion of a drug or a pharmaceutical agent in water with droplets of carbohydrate polymer has been disclosed (U.S. Pat. No. 4,713,249 and WO-84/00294). The major disadvantage of the procedure is that in many cases, a solubilizing organic co-solvent is needed for the encapsulation procedure. Removal of traces of such harmful co-solvents can lead to expensive manufacturing processes.

Recently, many successful stable dispersions of nanoparticulate drug or pharmaceutical compositions have been prepared by wet milling of the agent in the presence of surfactants, polymers, block polymers, and oligomers as a mixture thereof as surface modifiers to produce sterically stabilized dispersions of nanoparticulates with particle diameters less than 400 nm (U.S. Pat. No. 5,145,684, WPI 87-200422/29, EP 0,498,482 A2). This wet milling procedure still leads to the incorporation of solubilized heavy metals from the attrition of the milling media, which in many cases must be removed from the dispersion by tedious ion exchange procedures to formulate the final pharmaceutical product.

In a simultaneously filed application of Bagchi et al. (EK Docket 71,869) is described a method of microprecipitation of pharmaceutical agent from alkaline solution by neutralization with an acid. This invention leads to nanoparticulate dispersions of Z-average particle diameters less than 400 nm as measured by photon correlation spectroscopy. However, smaller average particle size of this pharmaceutical agent is more desirable as the smaller the size the greater is the bioavailability of the agent.

In another simultaneously filed application of Bagchi et al. (EK Docket 71,870) is described that the microprecipitation method can lead to further smaller size nanoparticulate pharmaceutical agent dispersions if precipitation is carried out in the presence of certain crystal growth modifiers (CGM).

In a separate simultaneously filed application (EK Docket 71872) is disclosed microprecipitation of micro-nanoparticulate dispension of pharmaceutical agents formed by chemical linkage between photographic couplers and known pharmaceutically useful drug or diagnostic agents. Such materials require specific special synthesis procedures to prepared.

It would be desirable to provide stable dispersible known pharmaceutical agent particles in submicron size range which can be readily prepared which do not appreciably flocculate or agglomerate due to interparticle attraction forces, and do not require the presence of a crosslinked matrix, simultaneously providing enhanced bioavailability of the drug. Furthermore, it would be highly desirable that such formulations do not involve removal of toxic residues such as toxic solvents or heavy metal solubilizates that arise out of attrition of the milling media.

SUMMARY OF THE INVENTION

We have discovered a novel method of preparing stable dispersions of drugs and other pharmaceutical agents in the presence of surface modifying and colloid stability enhancing surface active agents free of any trace of toxic solvents or solubilized heavy metal impurities by the following procedural steps:

1. Dissolving the said pharmaceutical agent in aqueous base with stirring,
2. Adding above #1 formulation with stirring to a mixture of surface active surfactant (or surface modifier) solution (slightly alkaline) to form a clear solution, and,
3. Neutralizing above formulation #2 with stirring with an appropriate acid solution. This procedure can be followed by;
4. Removal of formed salt by dialysis or diafiltration and
5. Concentration of dispersion by conventional means.

wherein the surface active surface modifier is a mixture of at least a nonionic and at least an anionic surfactant. The chemical structure, on a molecular basis, of at least one of the anionic surface active materials is at least on a molecular basis 75% identical to the pharmaceutical agent in question.

Figure 1:
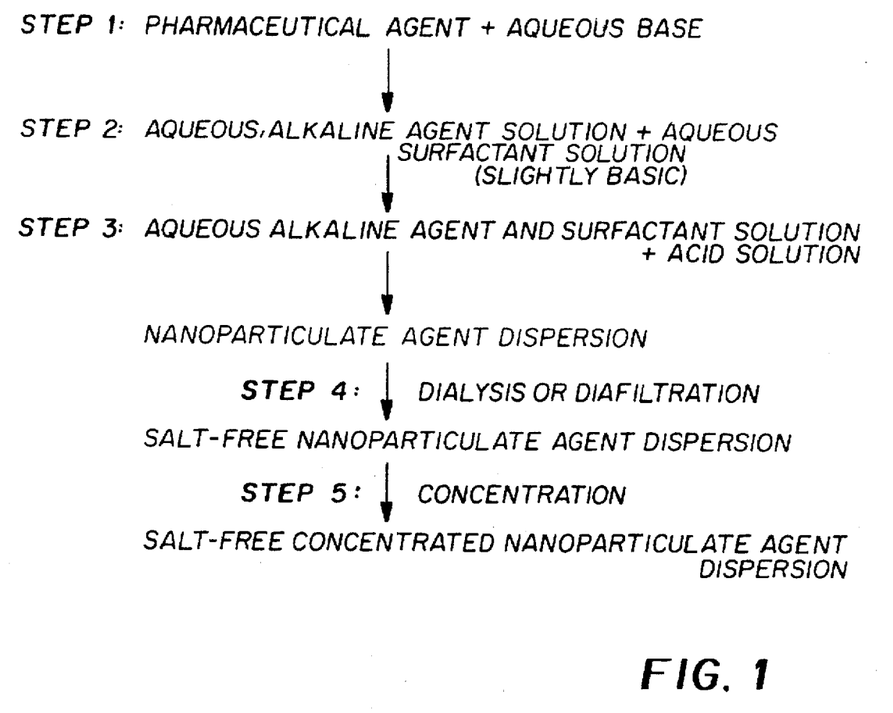
FIG. 1 Schematic for the microprecipitation of nanoparticulate pharmaceutical agents.

The process of this invention is illustrated in FIG. 1. The process of this invention produces dispersion of pharmaceutical agents with Z-average particle diameter less than 400 nm (as measured by photon correlation spectroscopy) that are stable in particle size upon keeping under room temperature or refrigerated conditions. Such dispersions also demonstrate limited particle size growth upon autoclave-decontamination conditions used for standard blood-pool pharmaceutical agents.

There can also be provided a pharmaceutical composition comprising the above-described particles and a pharmaceutically acceptable carrier thereof. Such pharmaceutical composition is useful in a method of treating mammals.

It is an advantageous feature that a wide variety of surface modified drug nanoparticles free of unacceptable contamination can be prepared in accordance with this invention.

Another particularly advantageous feature of this invention is that pharmaceutical compositions are provided exhibiting unexpectedly high bioavailability.

Still another advantageous feature of this invention is that pharmaceutical compositions containing poorly water soluble drug substances are provided which are suitable for intravenous administration techniques.

In other preferred embodiments of this invention, step 3 (FIG. 1) can be carried out in semicontinuous, continuous batch, or continuous methods at constant flow rates of the reacting components in computer-controlled reactors or in tubular reactors where reaction pH can be kept constant using pH-stat systems, as will be described in "Description of Preferred Embodiments." Advantages of such preferred modifications of this invention are clear in that they provide cheaper manufacturing procedures for large-scale production of nanoparticulate dispersion systems.

Another advantage of the invention is that unlike a milled dispersion, the final product is free of heavy metal contaminants arising from the milling media that must be removed due to their toxicity before product is formulated.

A further advantage of the method is that 5 unlike solvent precipitation, the final product of this invention is free of any trace of trace solvents that may be toxic and must be removed by expensive treatments prior to final product formulation.

Another advantage of this invention is that as 75% of the structure of the anionic surfactant is identical to the pharmaceutical agent, it retains many of the advantageous therapeutic or diagnostic characteristics of the agent itself, thus enhancing the efficacy of the formulated nanoparticulate composition. In general in any blood pool formulations, anionic surfactant concentration needs to be minimized and used in conjunction with a nonionic surfactant to shield the effect of the anionic charge. Unbound anionic surfactants are known to interact with physiological components such as cells, lipids and proteins to produce detrimental side effects. The anionic surfactant, of this invention, having 75% of its chemical composition identical to the agent, remains strongly attached to the nanoparticulate systems and thus less anionic surfactant remains available to produce detrimental side effects of the agent.

BRIEF DESCRIPTION OF THE DRAWINGS

FIG. 9 Cryo-transmission electron photomicrograph of nanoparticulate X-ray contrast agent "X" as prepared by the method of this invention in Example 1 (9a), Example 2 (9b) and Example 3 (9c).

FIG. 10 Particle size distribution of the dispersion of this invention of Example 1 (10a), Example 2 (10b), and Example 3 (10c).

DESCRIPTION OF PREFERRED EMBODIMENTS

This invention is based partly on the discovery that pharmaceutical agent particles having an extremely small effective average particle size can be prepared by homogeneous nucleation and precipitation in the presence of a mixture of certain surface modifiers, and that such particles are stable and do not appreciably flocculate or aggregate due to interparticle attractive force and can be formulated into pharmaceutical compositions exhibiting unexpectedly high bioavailability. While the invention is described herein primarily in connection with its preferred utility, i.e., with respect to nanoparticulate substances for use in pharmaceutical compositions, both therapeutic and diagnostic, it is also believed to be useful in other applications such as the formulation of particulate cosmetic compositions and the preparation of particulate dispersions for use in image and magnetic recording elements.

The particles of this invention comprise a pharmaceutical agent substance. The said agent substance exists as a discrete, crystalline phase. The crystalline phase differs from a non-crystalline or amorphous phase which results from precipitation techniques, such as described in EPO 275,796 cited above.

The invention can be practiced with a wide variety of pharmaceutical agent substances. The said agent substance preferably is present in an essentially pure form. The drug substance must be poorly soluble and dispersible in at least one liquid medium. By "poorly soluble" it is meant that the said substance has a solubility in the liquid dispersion medium of less than about 10 mg/mL, and preferably of less than about 1 mg/mL. A preferred liquid dispersion medium is water. However, the invention can be practiced with other liquid media in which a pharmaceutical agent is poorly soluble an dispersible including, for example, aqueous salt solutions, safflower oil, and solvents such as ethanol, t-butanol, hexane, and glycol. The pH of the aqueous dispersion media can be adjusted by techniques known in the art.

Suitable pharmaceutical agents can be selected from a variety of known classes of drugs including, for example, analgesics, anti-inflammatory agents, anthelmintics, antiarrhythmic agents, antibiotics (including penicillins), anticoagulants, antidepressants, antidiabetic agents, antiepileptics, antihistamines, antihypertensive agents, antimuscarinic agents, antimycobacterial agents, antineioplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminerigics (antiparkinsonian agents), haemostatics, immuriological agents, lipid regulating agents, muscle relaxants, parasympathomimetics, parathyroid calcitonin and biphosphonates, prostaglandins, radiopharmaceuticals, sex hormones (including steroids), antiallergic agents, stimulants and anoretics, sympathomimetics, thyroid agents, vasodilators and xanthines. Preferred drug substances include those intended for oral administration and intravenous administration. A description of these classes of pharmaceutical agents and a listing of species within each class can be found in Martindale, The Extra Pharmacopoeia, Twenty-ninth Edition, The Pharmaceutical Press, London, 1989, the disclosure of which is hereby incorporated by reference in its entirety. The drug substances are commercially available and/or can be prepared by techniques known in the art.

The particles of this invention contain a discrete phase of a said substance as described above having surface modifiers adsorbed on the surface thereof. Useful surface modifiers are believed to include those which physically adhere to the surface of the drug substance but do not chemically bond to the drug.

Suitable surface modifiers (the term "surface modifiers" is used interchangeably with "surfactants") can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, e.g., ethylene castor oil derivatives, polyoxyethylene sorbitan fatty acid esters, e.g., the commercially available Tweens, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, non-crystalline cellulose, magnesium aluminum silicate, triethanolamine, polyvinyl alcohol, and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986, the disclosure of which is hereby incorporated by reference in its entirety. The surface modifiers are commercially available and/or can be prepared by techniques known in the art.

Particularly preferred surface modifiers include polyvinyl pyrrolidone, Pluronic F68 and F108, which are block copolymers of ethylene oxide and propylene oxide, Tetronic 908, which is a tetrafunctional block copolymer derived from sequential addition of ethylene oxide and propylene oxide to ethylenediamine, dextran, lecithin, Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from JCI Specialty Chemicals, and Carbowax 3350 and 934, which are polyethylene glycols available from Union Carbide. Surface modifiers which have found to be particularly useful include polyvinylpyrrolidone, Pluronic F-68, and lecithin.

The surface modifiers are adsorbed on the surface of the pharmaceutical agent in an amount sufficient to maintain an effective Z-average particle size of less than about 400 nm as measured by photon correlation spectroscopy (PCS). The surface modifiers do not chemically react with the drug substance or itself. Furthermore, the individually adsorbed molecules of the surface modifier are essentially free of intermolecular crosslinkages.

In preferred embodiments of the invention, the effective average particle size is less than about 350 nm. In some embodiments, essentially all of the particles have a size less than 250 nm. When photon correlation spectroscopy (PCS) is used as the method of particle sizing the average particle diameter is the Z-average particle diameter known to those skilled in the art.

Additional surface modifier may be added to the dispersion after precipitation. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of agent substance and surface modifier can vary widely and the optimal amount of the surface modifier can depend, for example, upon the particular drug substance and surface modifier selected, the critical micelle concentration of the surface modifier if it forms micelles, etc. The surface modifier preferably is present in an amount of about 0.1–10 mg per square meter surface area of the drug substance. The surface modifier can be present in an amount of 0.1–90%, preferably 2–60% by weight based on the total weight of the dry particle.

The resulting dispersion of this invention is stable and consists of the liquid dispersion medium and the above-described particles. The dispersion of surface modified drug nanoparticles can be spray-coated onto sugar spheres or onto a pharmaceutical excipient in a fluid-bed spray coater by techniques well-known in the art.

Pharmaceutical compositions according to this invention include the particles described above and a pharmaceutically acceptable carrier therefore. Suitable pharmaceutically acceptable carriers are well-known to those skilled in the art. These include nontoxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the agent substance for treatment is effective to obtain a desired therapeutic response for a particular composition and method of administration. The selected dosage level therefore, depends upon the particular drug substance, the desired therapeutic effect, on the route of administration, on the desired duration of treatment and other factors. As noted, it is a particularly advantageous feature that the pharmaceutical compositions of this invention exhibit unexpectedly high bioavailability as illustrated in the examples which follow. Furthermore, it is contemplated that the drug particles of this invention provide more rapid onset of drug action and decreased gastrointestinal irritancy.

It is contemplated that the pharmaceutical compositions of this invention will be particularly useful in oral and parenteral, including intravenous, administration applications. It is expected that poorly water soluble drug substances; which prior to this invention, could not have been administered intravenously, may be administered safely in accordance with this invention. Additionally, drug substances which could not have been administered orally due to poor bioavailability may be effectively administered in accordance with this invention.

While the applicants do not wish to be bound by theoretical mechanisms, it is believed that the surface modifier hinders the flocculation and/or agglomeration of the particles by functioning as a mechanical or steric barrier between the particles, minimizing the close, interparticle approach necessary for agglomeration and flocculation. Alternatively, if the surface modifier has ionic groups, stabilization by electrostatic repulsion may result. It was surprising that stable drug particles of such a small effective average particle size and free of unacceptable contamination could be prepared by the method of this invention.

Representative illustrative species of substances useful in the practice of this invention include the X-ray contrast agent X ethyl-3,5-diacetoamido-2,4,6-triiodobenzoate or

X-Ray Contrast Agent "X"

Other illustrative examples of species of pharmaceutical contrast agents include the following compounds.

(diatrizoate) A.

(iothalamate) B.

(metrizoate) C.

and (iodipamide) D.

In the above structures, R can be OR', OH or alkylene or —O-alkylene wherein R' is alkyl, and $R^2$ and $R^3$ are independently H or alkyl. Each alkyl group can independently contain from 1-20, preferably 1-8, and more preferably, 1-4 carbon atoms. The alkylene group preferably contains from 1-4 carbons atoms such as methylene, ethylene, propylene and the like, optionally substituted with for example an alkyl group, such as methyl and ethyl.

Particularly preferred contrast agents include the ethyl ester of diatrizonic acid, i.e., ethyl-3,5-diacetamido-2,4,6-triiodobenzoate, also known as ethyl-3,5-bis(acetylamino)-2,4,6-triodobenzoate or tehyl diatrizoate, having the structural formula A above wherein $R=-OCH_2CH_3$ the ethyl glycolate ester of diatrizoic acid, i.e., ethyl(3,5-bis(acetylamino)-2,4,6-triiodobenzoyloxy)acetate, also known as ethyl diatrizoxyacetate, having the structural formula A above wherein and ethyl-2-(3,5-bis(acetylamino)-2,4,6-triiodobenzoyloxy) butyrate, also known as ethyl-2diatrizoxybutyrate, having the structural formula A above wherein In addition, it is expected that the invention can be practiced in conjunction with the water insoluble iodinated carbonate esters described in PCT/EP90/00053.

The above described X-ray contrast agents are known compounds and/or can be prepared by techniques known in the art. For example, water-insoluble esters and terminal amides of acids such as the above-described iodinated aromatic acids can be prepared by conventional alkylation or amidation techniques known in the art. The above-noted acids and other acids which can be used as starting materials are commercially available and/or can be prepared by techniques known in the art. The examples which follow contain illustrative examples of known synthetic techniques.

The particles useful in the practice of this invention include a surface modifier. Surface modifiers useful herein physically adhere to the surface of the X-ray contrast agent but do not chemically react with the agent or itself. Individually adsorbed molecules of the surface modifier are essentially free of intermolecular cross- linkages.

It is to be noted that agents (therapeutic or diagnostic) that are suitable for this invention must be soluble but remain relatively unhydrolyzed in aqueous alkaline solutions. Compounds described in U.S. Pat. No. 5,264,610, U.S. Pat. No. 5,260,478 (Bacon) and (application) PRF-469/92 (Bacon, et al.) that are unhydrolyzable in aqueous alkaline solutions are also included herein by reference as agents suitable for the practice of this invention.

The X-ray contrast agent can be an iodinated compound. The iodinated compound can be aromatic or nonaromatic. Aromatic compounds are preferred. The iodinated compound can comprise one, two, three, or more iodine atoms per molecule. Preferred species contain at least two, and more preferably, at least three iodine atoms per molecule. The iodinated compounds selected can contain substituents that do not impart solubility to the compound, such as, for example, alkylureido, alkoxyacylamido, hydroxyacetamido, butyrolactamido, succinimido, trifluoroacetamido, carboxy, carboxamido, hydroxy, alkoxy, acylamino, and the like substituents.

A preferred class of contrast agents includes various esters and amides of iodinated aromatic acids. The esters preferably are alkyl or substituted alkyl esters. The amides can be primary or secondary amides, preferably alkyl or substituted alkyl amides. For example, the contrast agent can be an ester or amide of a substituted triiodobenzoic acid such as an acyl, carbamyl, and/or acylmethyl substituted triiodobenzoic acid. Illustrative representative examples of iodinated aromatic acids include, but are not limited to, diatrizoic acid, metrizoic, iothalamic acid, trimesic acid, ioxaglic acid (hexabrix), ioxitalamic acid, tetraiodoterephthalic acid, iodipamide and the like. It is contemplated that poorly soluble derivatives of iodamide and iopyrol can be used herein.

The invention can also be practiced with poorly soluble derivatives, e.g., ester and ether derivatives, of hydroxylated nonionic X-ray contrast agents. Illustrative nonionic contrast agents include, but are not limited to, metrizamide; ioglunide; iopamidol; iopromide; iogulamide; iohexol, and other compounds described in U.S. Pat. No. 4,250,113; ioversol, and other compounds described in U.S. Pat. No. 4,396,598; nonionic triiodinated compounds, such as described in *Investigative Radiology*, Vol. 19, July-August 1984; and nonionic dimers, such as described in *Radiology*, 142: 115–118, January 1982. The invention can be practiced with poorly soluble derivatives of iodomethane sulfonamides, iodinated aromatic glucoanilides, 2-ketogulonamides, reversed amides, peptides, carbamates, esters, glycoside and glucose derivatives, benzamide derivatives, isophthalamides, bis compounds, and bispolyhydroxylated acylamides, such as described in Volume 73 of the *Handbook of Experimental Pharmacology*, entitled Radiocontrast Agents, edited by M. Sovak, 1984, Springer-Verlag, Berlin, pages 56–73.

Many of the iodinated molecules described above, if in monomeric form, can also be prepared as dimers (sometimes referred to as bis compounds), trimers (sometimes referred to as tris compounds), etc., by techniques known in the art. It is contemplated that this invention can be practiced with poorly soluble-iodinated compounds in monomeric, dimeric, trimeric and polymeric forms. Representative illustrative compounds are described by Sovak, cited above, pages 40–53.

In the practice of this invention, the microprecipitated dispersion contains several surface active surface modifiers. However, one of them has to be a nonionic surface active agent and one of the anionic surface active material must have a chemical structure that has 75% structural identity on a molecular basis with the pharmaceutical agent in question. The charge moiety may be a —$SO_3$—, —$SO_4$—, on —COO— group. A carboxylated compound is preferred as such a group is a week acid group leading to the weaker interactions with physiological components such as cells, lipids and proteins. Furthermore a carboxylated material is ionized in basic conditions just prior to microprecipitation and upon neutralization with acids after precipitation becomes substantially protonated, minimizing the charge interactions with physiological components. The pharmaceutical agent of this invention could be a therapeutic or a diagnostic agent. For example, X-ray contrast agent "X", described earlier is a diagnostic agent which we have used throughout this present invention as an illustrative example of the instant invention. Therefore, in the following we provide a list of chemical structures of the anionic surface active material of this invention that has at least 75% structural similarity with the agent in question, i.e., X-ray contrast agent "X". The preferred anionic surfactant of this invention is Sodium Diatrazoate (DA) shown in structure "Y".

Anionic Surfactant "Y"

Wherein M is a monovalant cation such as Na$^+$, K$^+$, Rb$^+$, Cs$^+$, NH$_4{}^+$, or H$^+$. The anionic surface active material of this invention may be present in amount of 0.1 to 40%, preferably between 0.1 to 20% based on the weight of the pharmaceutical agent in addition to other nonionic and/or anionic surface active substances as indicated earlier. By the term "structurally identical on a molecular basis" is meant that the structures are identical atom for atom and in their sequential connectivities to each other.

METHODS OF PERFORMING THE INVENTION

The process of this invention involves a method of preparing stable dispersions of pharmaceutical agents in the presence of a surface modifying and colloid stability-enhancing surface active agents free of trace of any toxic solvents or solubilized heavy metal impurities by the following procedural steps.

1. Dissolving the said pharmaceutical agent in aqueous base with stirring,
2. Adding above #1 formulation, with stirring, to a solution of a mixture of slightly basic surface active surfactants (or surface modifiers) to form a clear solution and,
3. Neutralizing above formulation, with stirring, #2 with an appropriate acid solution and optionally,
4. Removal of the salts by diafiltration or dialysis and
5. Concentration of dispersion by conventional means.

The mixture of surfactants contains at least a nonionic surfactant and an anionic surfactant that is structurally on a molecular basis, at least 75% identical to the pharmaceutical agent.

The process of this invention is illustrated in FIG. 1. The process of this invention produces dispersions of pharmaceutical agent with Z-average particle diameter, less than 400 nm (as measured by PCS) that are stable in particle size upon keeping under room temperature or refrigerated conditions. Such dispersions also demonstrate limited particle size growth upon autoclave decontamination conditions used for standard blood-pool pharmaceutical agents.

This invention can also be performed in semicontinuous, continuous, or continuous batch methods. Such methods provide numerous advantages over prior processes of forming dispersions of pharmaceutical agents. The invention provides continuous or semicontinuous methods in which the particle size of the formed dispersions will be reproducible from run to run. Shutdowns of the system can be accomplished with minimum waste or growth of particle size. These and other advantages of the invention will become apparent from the detailed description below.

Figure 2:
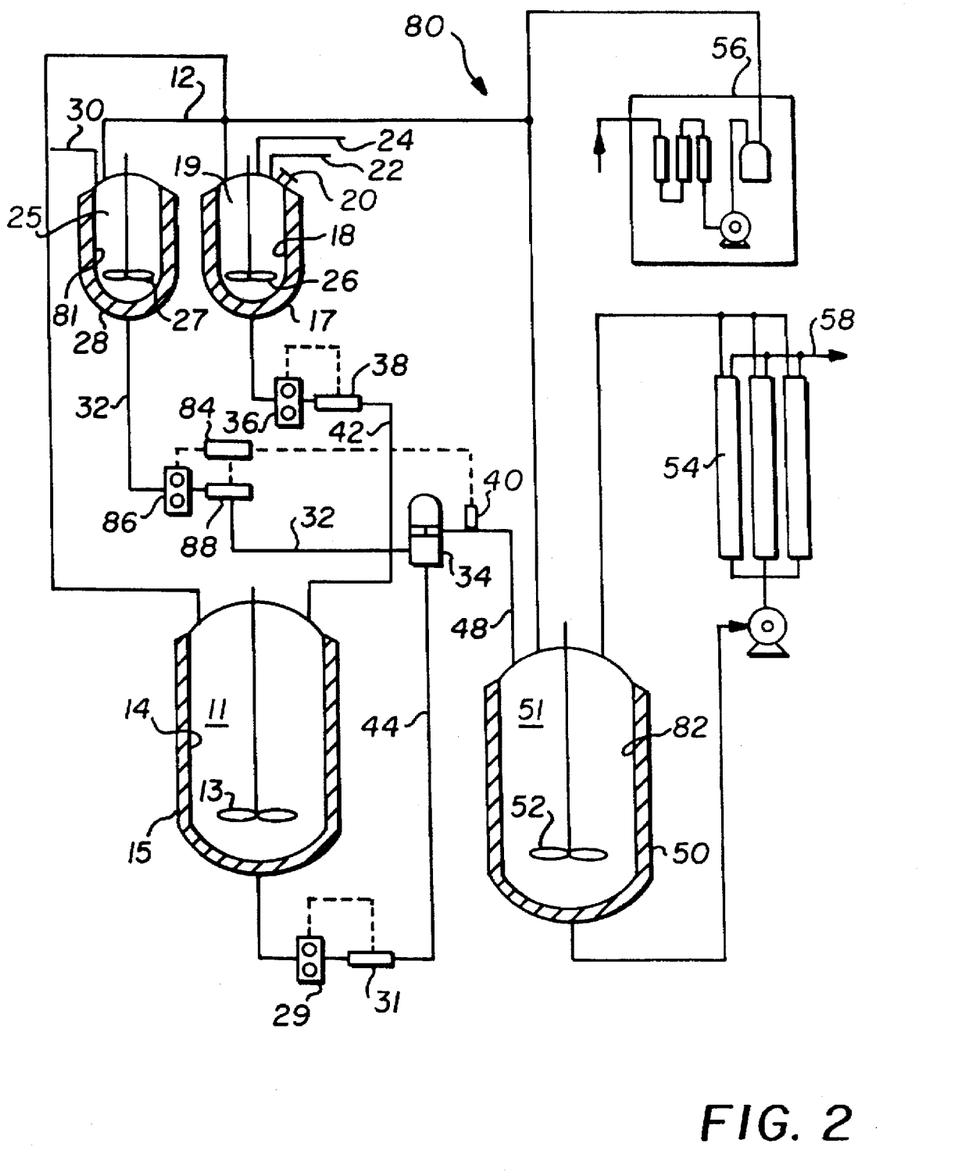
FIG. 2 Schematic for large-scale manufacture of nanoparticulate pharmaceutical agents.

The schematic of FIG. 2 illustrates apparatus 80 for performing the process of the invention. The apparatus is provided with high purity water delivery lines 12. Tank 14 contains a solution 11 of surfactants and high purity water. Jacket 15 on tank 14 regulates the temperature of the tank. Surfactants enter the tank through line 16. Tank 18 contains a pharmaceutical agent solution 19. Jacket 17 controls the temperature of materials in tank 18. The tank 18 contains a port for delivery of the pharmaceutical agent entering through manhole 20, a base material such as aqueous sodium hydroxide solution entering through line 22. The solution is maintained under agitation by the mixer 26. Tank 81 contains acid solution 25 such as propionic acid solution entering through line 30. The tank 81 is provided with a heat jacket 28 to control the temperature, although with the acids normally used, it is not necessary. In operation, the acid solution is fed from tank 81 through line 32 to mixer 34 via the metering pump 86 and flow meter 88. A pH sensor 40 senses the acidity of the dispersion as it leaves mixer 34 and allows the operator to adjust the acid pump 86 to maintain the proper pH in the dispersion exiting the mixer 34. The pharmaceutical agent 19 passes through line 42, metering pump 36, flow meter 38, and joins the surfactant solution in tank 14. In tank 14, the alkaline pharmaceutical agent is mixed with the surfactant solution and is pumped using pump 29 and flow meter 31 into the mixing chamber 34.

The particles are formed in mixer 34 and exit through pipe 48 into the ultrafiltration tank 82. In the preferred process, tank 82, the dispersion 51 is held while it is washed by ultrafiltration membrane 54 to remove the salt from solution and adjust the material to the proper water content for makeup at the proper concentration. The source of high purity water is purifier 56. Agitator 13 agitates the surfactant solution in tank 14. Agitator 27 agitates the acid solution in tank 81. The generated salts are removed during the ultrafiltration process through permeate (filtrate) stream 58.

In some instances, one of the suitable surface modifier is an ester that may be base hydrolyzable. An example of such surfactant is Aerosol A102 or Aerosol A103, manufactured by American Cyanamid.

Aerosol A102 ⟹ where m = 10–12, n = 3–5

Aerosol A103 ⟹ where n = 5–10

In a preferred embodiment, the above procedure is followed with step 4 which comprises removing the formed salts and solvent by diafiltration or dialysis. This is done in the case of dialysis by a conventional dialysis device known in the art. In the case of diafiltration the process is carried out in a conventional diafiltration device known in the art. Preferrably, the final step is concentration to a desired concentration of the agent dispersion. This is done by a conventional diafiltration device known in the art.

During small-scale laboratory precipitation scheme described in FIG. 1, preparation time is short enough such that hydrolysis of the surfactant in alkaline solution is virtually undetectable. However, during manufacturing, mixing and holding time could extend to 1–2 hours. In such case, hydrolysis of the surfactant is substantial and needs to be eliminated by reducing the contact time of the surfactant with the alkali. To accomplish this, the following manufacturing schemes are adopted.

In the following embodiment of the invention, the alkaline pharmaceutical agent solution is mixed with the surfactant solution continuously and neutralized within less than a second of mixing in a continuous reactor with acid solution to eliminate surfactant hydrolysis.

Figure 3:
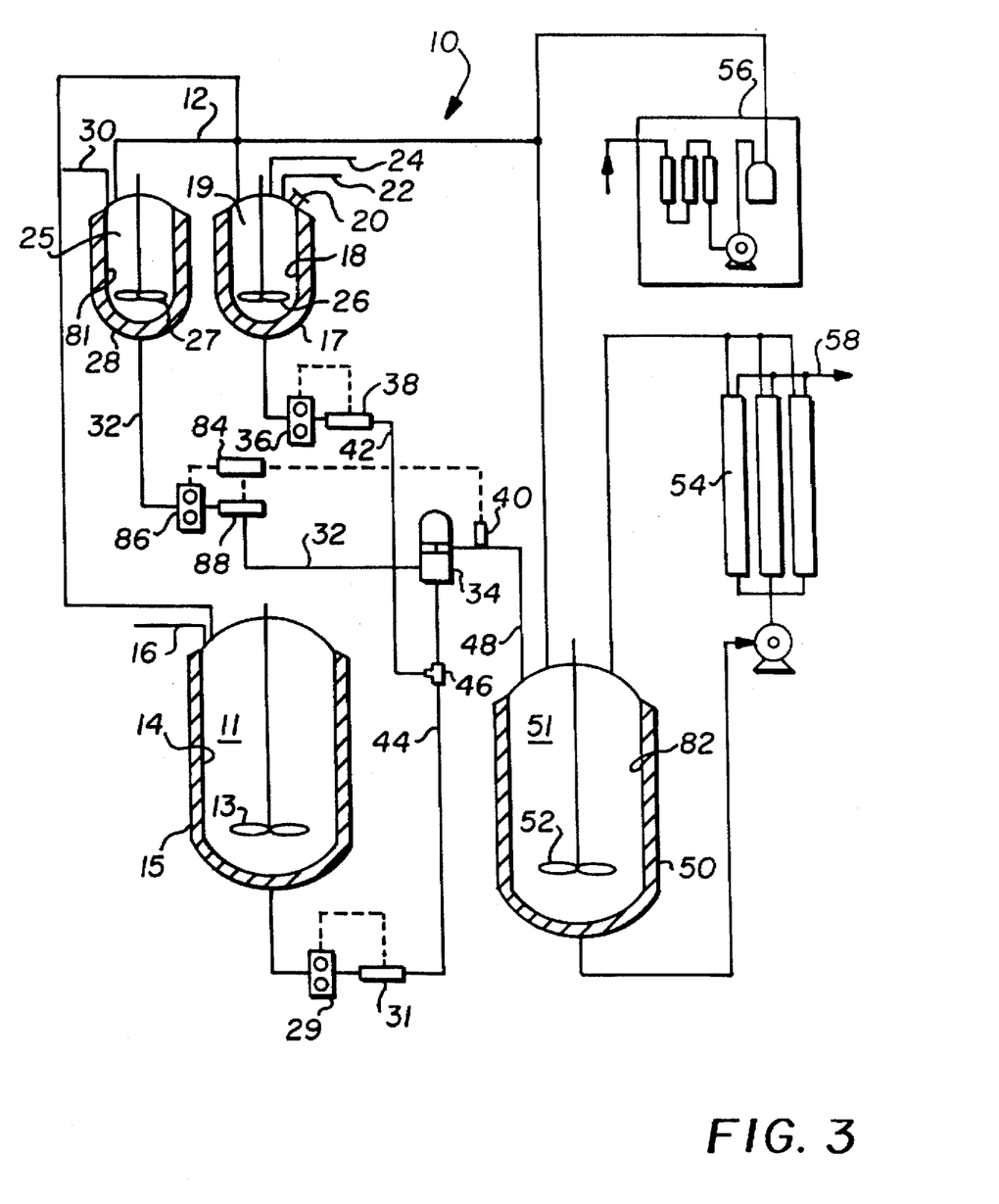
FIG. 3 Schematic for large-scale manufacture of nanoparticulate pharmaceutical agents using base hydrolyzable surface modifying compounds.

The schematic of FIG. 3 illustrates apparatus 10 for performing the process of the invention. The apparatus is provided with high purity water delivery lines 12. Tank 14 contains a solution 11 of surfactants and high purity water. Jacket 15 on tank 14 regulates the temperature of the tank. Surfactants enters the tank through line 16. Tank 18 contains a pharmaceutical agent solution 19. Jacket 17 controls the temperature of materials in tank 18. The tank 18 contains a port for delivery of the pharmaceutical agent entering through manhole 20, a base material such as aqueous sodium hydroxide solution entering through line 22. The solution is maintained under agitation by the mixer 26. Tank 81 contains acid solution 25 such as propionic acid entering through line 30. The tank 81 is provided with a heat jacket 28 to control the temperature, although with the acids normally used, it is not necessary. In operation, the acid is fed from tank 81 through line 32 to mixer 34 via the metering pump 86 and flow meter 88. A pH sensor 40 senses the acidity of the dispersion as it leaves mixer 34 and allows the operator to adjust the acid pump 86 to maintain the proper pH in the dispersion exiting the mixer 34. The pharmaceutical agent 19 passes through line 42, metering pump 36, flow meter 38, and joins the surfactant solution in line 44 at the "T"-fitting 46. The particles are formed in mixer 34 and exit through pipe 48 into the ultrafiltration tank 82. In tank 82, the dispersion 51 is held while it is washed by ultrafiltration membrane 54 to remove the salt from solution and adjust the material to the proper water content for makeup at the proper concentration. The source of high purity water is purifier 56. Agitator 13 agitates the surfactant solution in tank 14. Agitator 27 agitates the acid solution in tank 81. The generated salts are removed during the ultrafiltration process through permeate (filtrate) stream 58.

In some cases, the alkaline pharmaceutical agent, the surfactant solution, and the acid solution may be directly and continuously mixed in the continuous mixer to obtain nanoparticulate dispersions. In such a case, the following manufacturing scheme is adopted.

Figure 4:
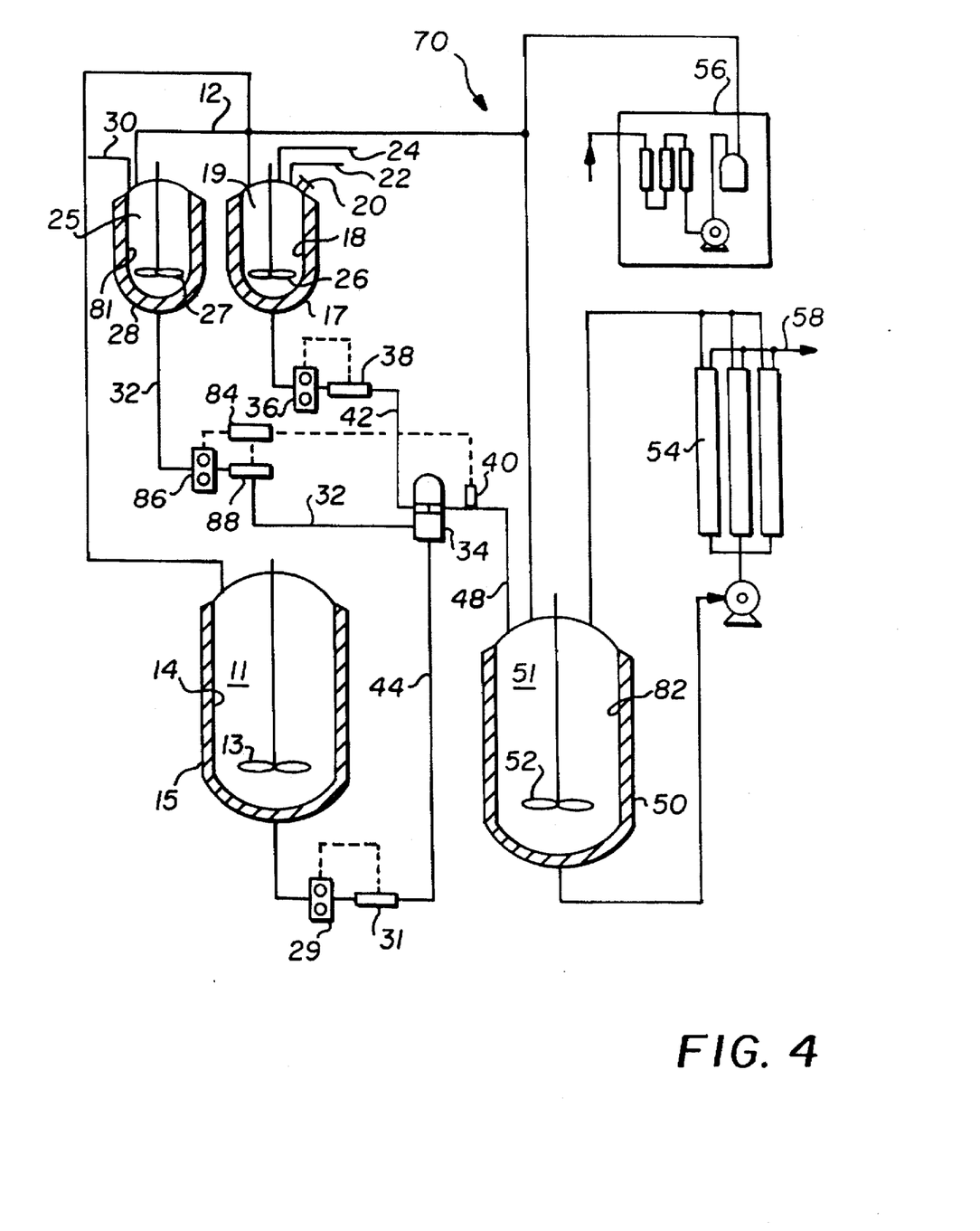
FIG. 4 Schematic for large-scale manufacture of nanoparticulate pharmaceutical agents using base hydrolyzable surfactants by continuous direct mixing.

The apparatus 70 schematically illustrated in FIG. 4 is similar to that illustrated in FIG. 3 except that the acid solution in pipe 32, the surfactant solution in pipe 44, and the pharmaceutical agent solution in pipe 42 are directly led to mixing device 34. Corresponding items in FIG. 3 and FIG. 4 have the same numbers. In this system, all mixing takes place in the mixer 34 rather than joining of the surfactant solution and the pharmaceutical agent solution in the "T"-connection immediately prior to the mixer as in the FIG. 3 process.

Figure 5:
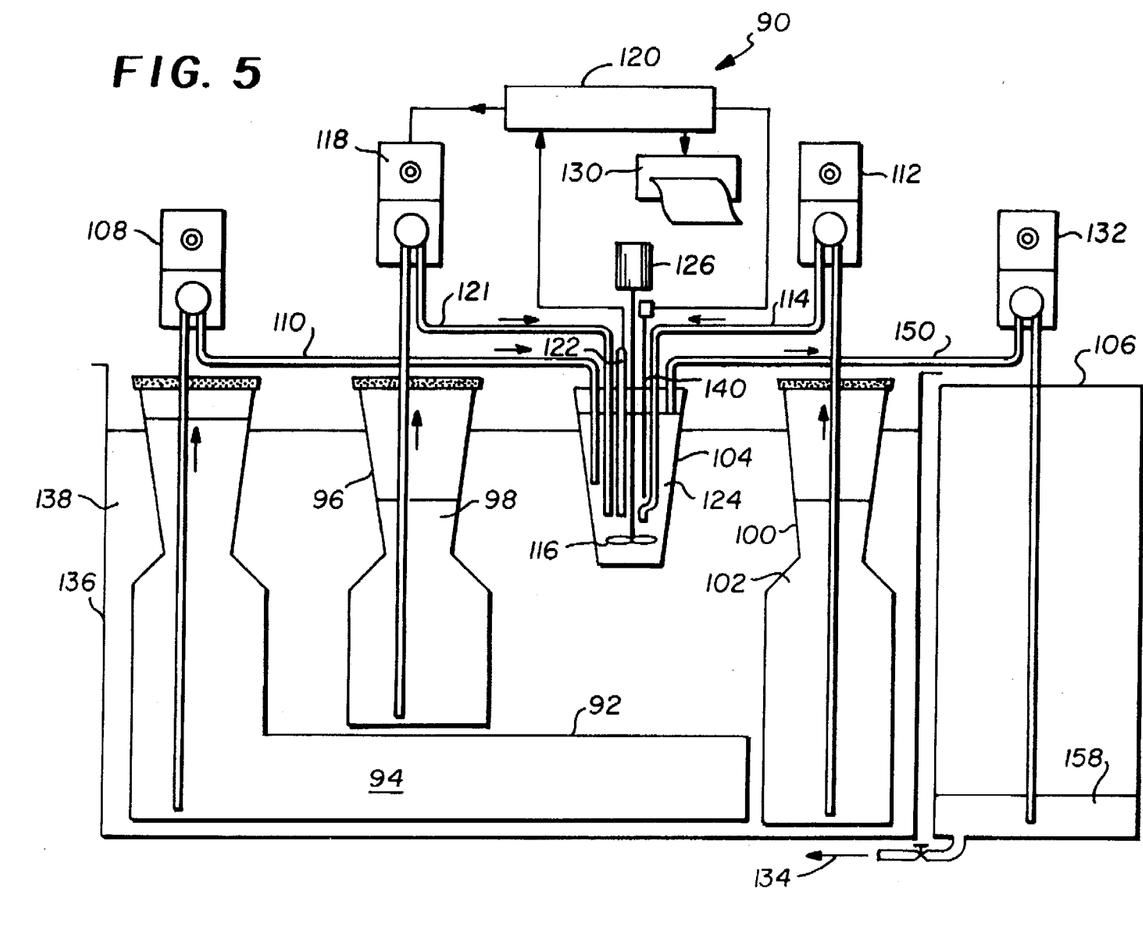
FIG. 5 Schematic for the small-scale pH-controlled microprecipitation device.
Figure 6:
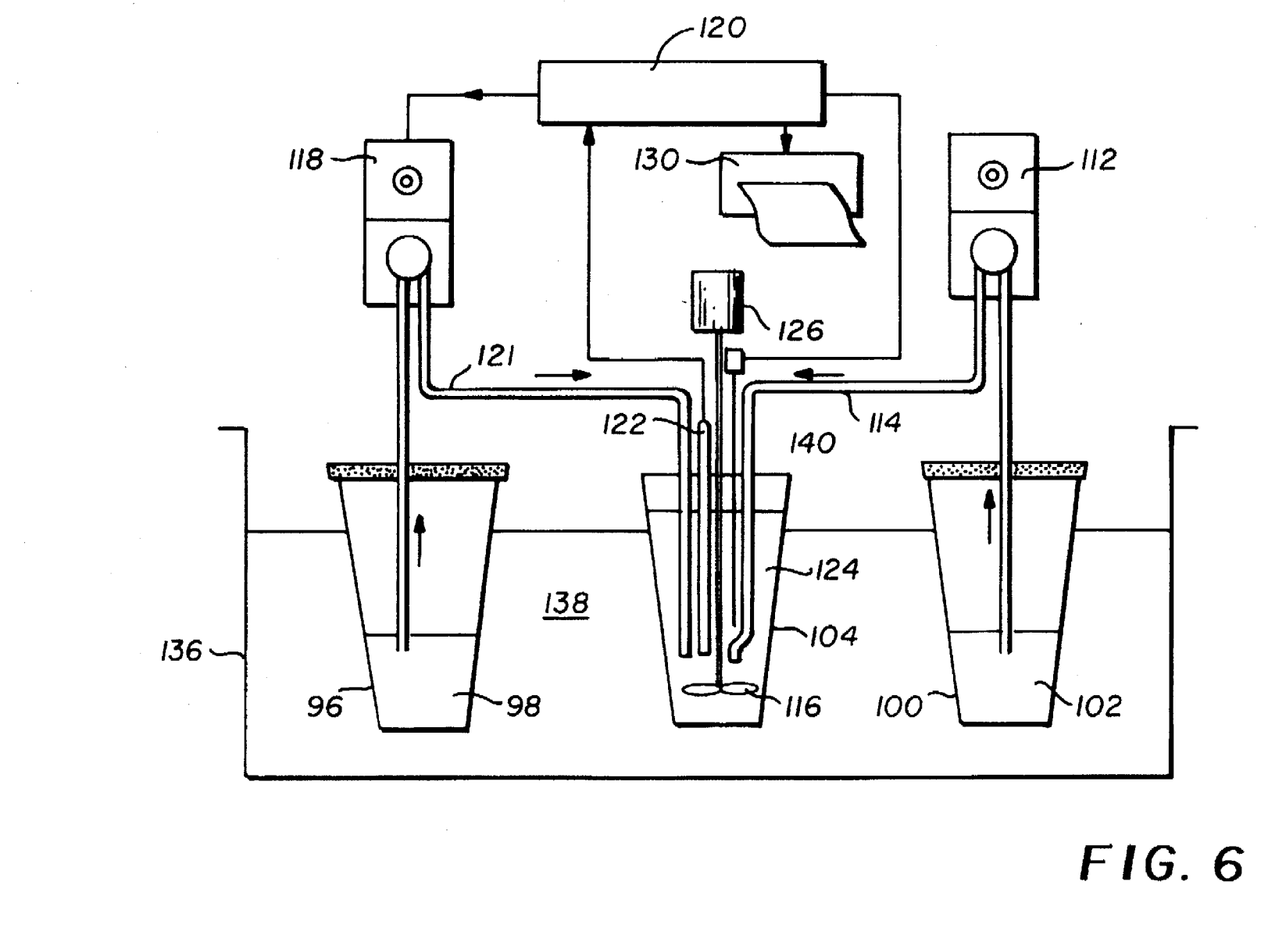
FIG. 6 Schematic for the larger-scale pH-controlled microprecipitation device.

The previously described methods of this invention find their most preferred use in large-scale production such as in a continuous commercial process. However, preparation of dispersions in pH-controlled conditions can also be practiced on a smaller and/or slower scale in a semicontinuous or continuous manner. The devices of FIGS. 5 and 6 illustrate equipment that is in accordance with the invention for smaller scale production. The device of FIG. 5 was designed for continuous pH-controlled precipitation of dispersions. The apparatus 90 of FIG. 5 provides a continuous means for precipitation of nanoparticulate dispersions. Container 92 is provided with an aqueous surfactant solution 94. Container 96 is provided with an acid solution. Container 100 contains a basic solution 102 of the pharmaceutical agent. Container 104 provides a mixing and reacting chamber where the dispersion formation takes place. Container 106 is a collector for the dispersed suspensions 158. In operation, the surfactant solution 94 is metered by pump 108 through line 110 into the reactor vessel 104. At the same time, the basic pharmaceutical agent solution is metered by pump 112 through line 114 into the reactor 104 at a constant predetermined rate. The solutions are agitated by stirrer 116, and acid 98 is metered by pump 118 through line 121 into the reactor 104 to neutralize the solution. The pumping by metering pump 118 is regulated by controller 120. Controller 120 is provided with a pH sensor 122 that senses the pH of the dispersion 124 in reactor 104 and controls the amount and the rate of the addition of acid 98 added by pump 118 to neutralize the content of the reaction chamber. The drive for stirrer 116 is 126. The recorder 130 constantly records the pH of the solution to provide a history of the dispersion 124. Metering pump 132 withdraws the dispersion solution from reactor 104 and delivers it to the container 106 using pump 132 and line 150 where it may exit from the outlet 134. In a typical precipitation, there is a basic pharmaceutical agent solution 102, sodium hydroxide solution, and the surfactant solution. The surfactants are in water, and the neutralizing acid is an aqueous solution of acetic or propionic acid. The reaction chamber has a capacity of about 800 mL. Pharmaceutical agent solution tank 100 has a capacity of about 2500 mL. The surfactant solution tank 92 has a capacity of about 5000 mL. The acid solution tank has a capacity of about 2500 mL, and the dispersion collection tank has a capacity of about 10,000 mL. The temperature is controlled by placing the four containers 92, 96, 104, and 100 in a bath 136 of water 138 whose temperature can be regulated to its temperature up to 100 ° C. Usually, precipitation is carried out at 25° C. The temperature of the bath 138 is controlled by a steam and cold water mixer (not shown). The temperature probe 140 is to sense the temperature of the reactor. This is necessary for correct pH reading. The neutralization of the basic pharmaceutical agent solution in the reaction chamber 104 by the proportionally controlled pump 118 which pumps in acid solution 98 results in control of pH throughout the run to ±0.2 of the set pH value which is usually about 6.0.

FIG. 6 schematically illustrates a semicontinuous system for forming nanoparticulate dispersions of pharmaceutical materials. Identical items are labeled the same as in FIG. 5. Because of reduced scale, the sizes of acid kettle 96 and the pharmaceutical agent kettle 100 are smaller (about 800 mL each). In the system of FIG. 6, the reactor 104 is initially provided with an aqueous surfactant solution. In this is pumped a basic solution of photographic agent 102 through pipe 114. 112 is a pH sensor that, working through controller 120, activates pump 118 to neutralize the dispersion to a pH of about 6 by pumping acetic acid 98 through metering pump 118 and line 121 to the reactor 104. Reactor 104 must be removed, dumped, and refilled with the aqueous surfactant solution in order to start a subsequent run.

The base used to solubilize the photographic agent could be any strong alkali as $NH_4OH$, NaOH, KOH, LiOH, RbOH, or CsOH, or organic bases as amines such as trialkyl amines or pyridine, etc.

The acids used for neutralization in this invention preferably could be any weak acids such as formic, acetic, propionic, butyric acids, etc., or in some cases, mineral acids such as HCl, $H_2SO_4$, $HNO_3$, $HClO_4$, may be preferred.

Other modifications of this invention could be performed according to the processes described in other patents of Bagchi, et al., such as U.S. Pat. Nos. 4,933,270; 4,970,131; 4,900,431; 5,013,640; 5,089,380; 5,091,296; 5,104,776; 5,135,884; 5,158,863; 5,182,189; 5,185,230; 5,264,317; 5,279,931; 5,358,831 and are hereby incorporated herein by reference.

Figure 7:
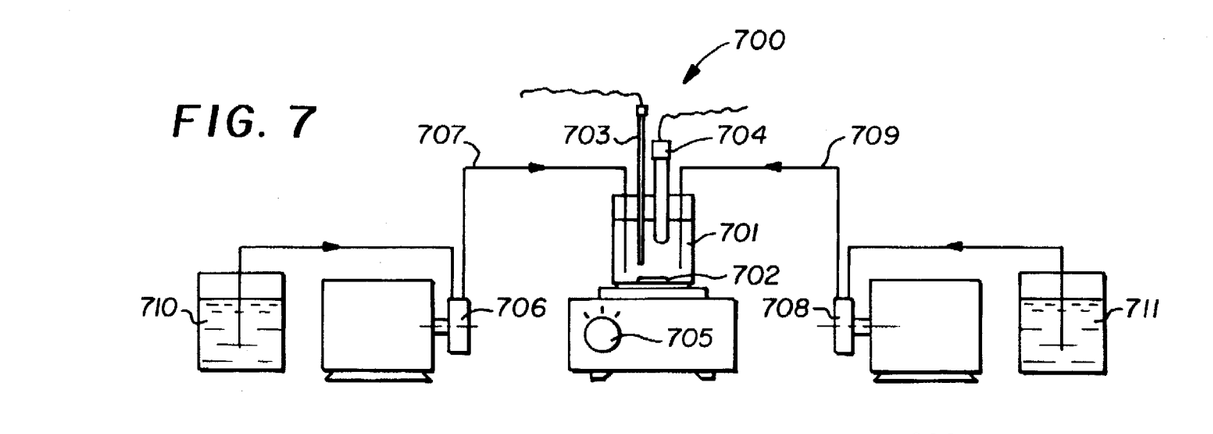
FIG. 7 Schematic for alternate small-scale precipitation of pharmaceutical agents.

Another preferred modification of the precipitation device of this equipment, 700, of this invention is shown in FIG. 7. FIG. 7 schematically depicts a batch system for precipitating crystalline nanoparticulate pharmaceutical agent suspensions. The reactor 701 is initially provided with an aqueous solution of surfactant, or a surface modifier and pH buffer. The reactor is equipped with a magnetic stirring bar 702, a temperature probe 703, and a pH sensor 704. The revolutions of the magnetic stirring bar are maintained at a medium-high level, as controlled by a magnetic plate regulator 705. A strongly basic, particle-free aqueous solution of the pharmaceutical agent is delivered by a pump, 706, with a flow rate control, via tubing 707, to the reactor. Simultaneously, an aqueous acid solution is delivered to the reactor by a pump 708 with a flow rate control via tubing 709. The flow rate of both streams, their concentration, and the duration of their subsurface delivery are carefully selected in such a manner that the final pH is restricted between 3.0 and 7.0, and the final concentration of the suspension is between 0.5% to 10%. Containers 710 and 711 hold the pharmaceutical agent solution and acid solution, respectively.

Figure 8:
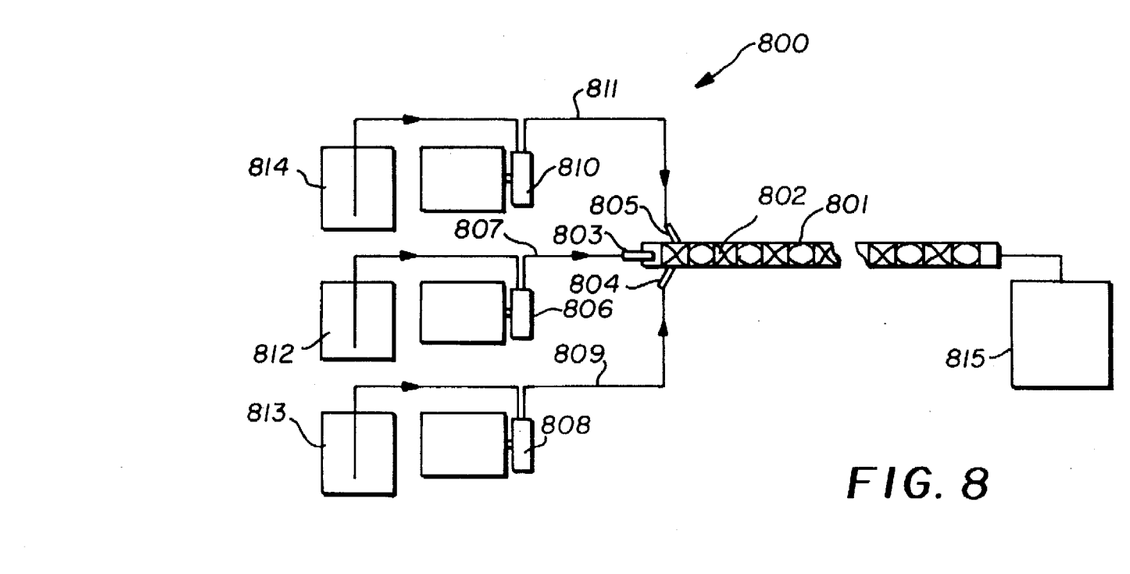
FIG. 8 Schematic of continuous tubular microprecipitation device of this invention.

In another preferred embodiment of the invention continuous precipitation may be carried out in a tubular reactor 800 of FIG. 8. The neutralization reaction takes place in a tubular reactor, which consists of a tubing or pipe 801 equipped with a static mixer 802. The inlet section of the tubular reactor allows for an influx of three streams through three connectors 803, 804, and 805. Initially, the tubular reactor is supplied with a stream of an aqueous carrier solution of surfactants and pH adjusting buffer, by a pump 806, with a flow rate control, via tubing 807, and the connector 803. A strongly basic, particle-free aqueous solution of the pharmaceutical agent is delivered by a pump 808 with a flow rate control, via tubing 809 and the connector 804, to the tubular reactor. Simultaneously, an aqueous acid solution is delivered to the reactor by a pump with a flow rate control 810, via tubing 811 and the connector 805. The flow rate of the influx streams and their concentration are selected in such a manner that the final pH is less than 7.0, and preferably is between 3.0 and 7.0, and the final concentration of the suspension is between 0.5% to 10%. Containers 812, 813, 814, and 815 hold carrier solution, pharmaceutical agent solution, acid solution, and the product suspension, respectively. The total length of the tubular reactor is such that the reaction is completed before the suspension reaches the outlet of the reactor, at the flow rates of the influx streams and the diameter of the reactor used. In an alternate embodiment of the above apparatus, only two inlet streams are simultaneously delivered to the tubular reactor. The connector 803 is plugged off, and the pump 806 is not shut off. Since the carrier solution is not used, the aggregate volumetric flow rate of the two reactant streams is higher than that typically employed in the three-stream configuration described above.

EXAMPLES

The invention is illustrated in the following examples.

Examples 1 through 3

Two repeat preparations of nanoparticulate dispersions of X-ray contrast agent "X" were prepared (Examples 1 and 2) using the anionic surface active material "Y" of this invention. Twenty grams of compound "X" was dissolved in 20 g of distilled water and 45 g 20% NaOH by heating to 75° C. The solution was cooled to room temperature. The surfactant solution was prepared by dissolving 6.5 g Tetronic T-908 (BASF), 0.4 g of sodium diatrazoate (compound "Y") in 500 g of distilled water made slightly basic with the addition of 1 g of 20% NaOH solution. The first solution containing compound "X" was added to the second surfactant solution to form a clear solution. The latter was then neutralized with 300 g of 15% propionic acid to form the nanoparticulate dispersion of compound "X". The dispersion was then dialyzed against a continuos flow of distilled water for 24 h to remove the formed salts. The dialysis bag was then hung in a well ventilated hood for a week to concentrate the dispersion to contain about 10% of compound "X".

Figure 9A:
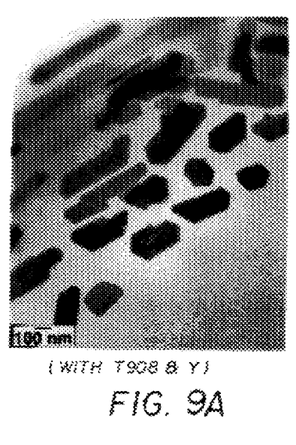
Figure 9B:
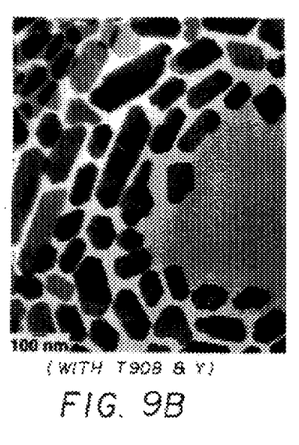

FIGS. 9a and 9b show the cryo-transmission photoelectron micrographs of particles of the two dispersions of Examples 1 and 2.

The dispersion of X-ray contrast agent "X" of Example 3 was prepared much in the same manner, except the contents of this various solution were as follows:

Agent solution:
compound "X"—12 g
distilled water—12 g
20% NaOH solution—27 g

The agent solution was dissolved at 75° C. and then cooled to room temperature.

Figure 9C:
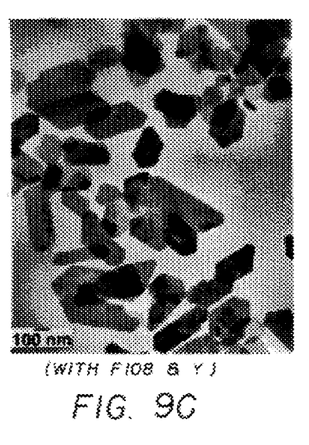

Surfactant solution:
distilled water—300 g
F-108 (BASF)—3.9 g
surfactant "Y"—0.24 g
20% NaOH solution—0.6 g Acid solution:
15% ropronic acid—180 g Using the above solutions and the method of FIG. 1 as before, the nanoparticulate dispersion of compound "X" of Example 3 was prepared. The dispersion was dialyzed continuously against distilled water in a dialysis tank and was concentrated to about 10% of compound "X" by hanging the dialysis bag in a well ventilated hood for seven days to evaporate the exuding water. FIG. 9c shows a cryo-transmission electron micrograph of the formed particles.

Figure 10A:
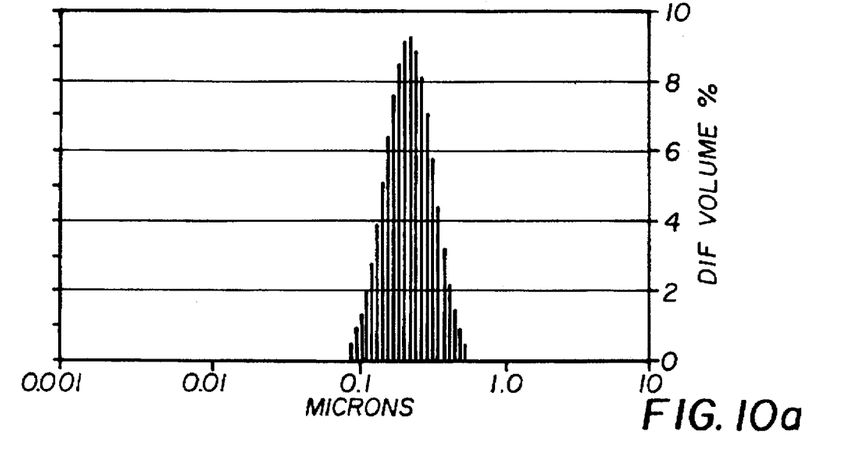
Figure 10B:
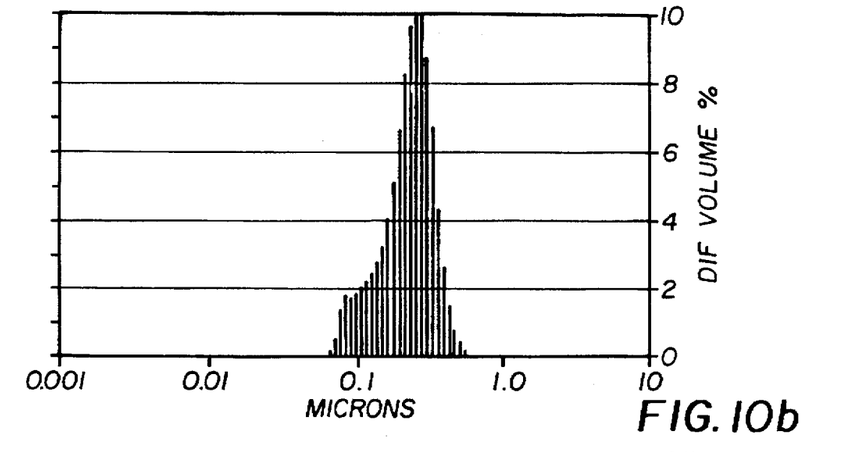
Figure 10C:
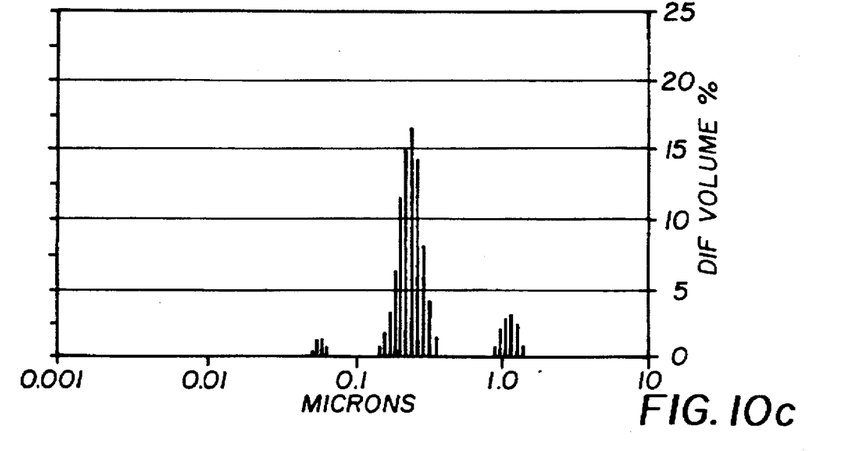

The particle size distributions of all the dispersions of Examples 1, 2, and 3 are shown in FIGS. 10a, 10b, and 10c, respectively as determined by PCS. It is observed in FIG. 10 that the major peak of the distribution of all these dispersions lie around 250 nm in diameter. The Z-average particle size of the three dispersions determined by photon correlation spectroscopy (PCS) and are shown in Table I. The dispersions were subjected to an autoclave treatment at 120° C. for 25 min to determine effect of sterilization. After autoclaving, the Z-average particle diameters were also determined and are also shown in Table I.

TABLE I

Physical Characteristics of Microprecipitated
Nanoparticulate Dispersions of Compound X

| Example | Surface Modifying Surfactnats | PCS Particle Diameter, Z-Av. nm | |
|---|---|---|---|
| | | Initial | After Autoclaving |
| 1 | T-908 + Y | 227 | 368 |
| 2 | T-908 + Y | 235 | 390 |
| 3 | F-108 + Y | 253 | 284 |

It is seen in Table I that all the dispersions seem to be substantially stable to autoclave treatment exibiting only small growth of particle diameter. Even after anutoclaving the particle size of all the dispersions remain less than 400 nm in diameter.

Lymphographic imaging using nanoparticulate compound "x" was achieved as follows:

The suspension of Example 3 was used to image the lymph system (approximately 3 Kg rabbits) by computed tomography (CT). The suspension was dosed by percutaneous administration via the foot pads of the rabbits at 0.03 mL/Kg animal body weight and imaged 9 h after administration. The CT images demonstrated enhanced X-ray contrast of the lymph nodes responsible for clearance from the anatomical areas of the rabbit injected with this formulation. Enhanced density was observed for times as long as 1 week after which the X-ray density of the lymph nodes returned to normal levels.

The invention has been described in detail with reference to preferred embodiments thereof, but it will be understood that various variations and modifications can be effected within the spirit and scope of the invention.

We claim:

1. A microprecipitation process of forming nanoparticulate dispersions of pharmaceutical agents comprising:

a first step of dissolution of the pharmaceutical agent in aqueous base, a second step of adding to step a an aqueous solution of slightly alkaline mixture of at least one nonionic surface active surface modifier and at least one anionic surface active surface modifier and a third step of neutralizing the formed alkaline solution with an acid to form a dispersion, wherein the said anionic surface active surface modifier is structurally on a molecular basis at least 75% identical to the chemical structure of the pharmaceutical agent.

2. The process of claim 1 wherein the pharmaceutical agent is selected from:

therapeutic agent and diagnostic agent.

3. The process of claim 1 wherein the nanoparticulate dispersion is characterized by a Z-average particle diameter less than 400 nm as measured by photon correlation spectroscopy.

4. The process of claim 1 wherein the base is selected from any one or a combination of the following:

NaOH

KOH

CsOH trialkyl amines and pyridine.

5. The process of claim 1 wherein the neutralizing acid is selected from:

a weak acid and a strong acid.

6. The process of claim 1 wherein the neutralizing acid is selected from any one of the following:

HCl $HNO_3$ $HClO_4$ $H_2SO_4$ formic acid propionic acid acetic acid and butyric acid.

7. The process of claim 1 wherein the surface modifier is a mixture selected from the following:

an anionic surfactant a nonionic surfactant a polymeric molecule and an oligomeric molecule.

8. The process of claim 1 wherein the concentration of the dispersion is achieved by any one of the methods selected from the following:

diafiltration dialysis and evaporation.

9. The process of claim 1 wherein the nanoparticulate dispersion is characterized by a Z-average particle diameter less than 300 nm a measured by photon correlation spectroscopy.

10. The process of claim 1 wherein the pharmaceutical agent is an X-ray contrast agent.

11. The process of claim 1 wherein the nanoparticulate pharmaceutical agent is concentrated to contain anywhere between 2 to 20% of the agent.

12. The method of claim 1 practiced in any mode selected from the following:

a batch process, a semicontinuous batch process, and a continuous process.

13. The method of claim 1 wherein the anionic surface active surface modifier is present at a level of 0.1 to 40% by weight of the pharmaceutical agent.

14. The method of claim 1 wherein the anionic surface active surface modifier is present at a level of 0.1 to 20% by weight of the pharmaceutical agent.

15. The process of claim 1 wherein step 3 is followed by step 4 which removes the salts by diafiltration or dialysis and step 5 wherein the dispersion is concentrated to desired concentration of the agent dispersion.

16. A microprecipitation process of preparing nanoparticulate dispersions of a pharmaceutical agent comprising:

continuously providing a first solution of a pharmaceutical agent in aqueous base, a second flow of an equeous solution comprising at least one nonionic surface active surface modifier and at least one anionic surface active surface modifier and, continuously providing a third flow of an acid solution at a constant desired pH to form a nonoparticulate pharmaceutical agent dispersion, followed by a step of removal of the formed salts and then a step of concentrating the said dispersion to a desired level, wherein, the said nonionic surface active surface modifier is structurally on a molecular basis at least 75% identical to the chemical structure of the pharmaceutical agent.

17. The method of claim 16 wherein step 4 comprises diafiltration.

18. The method of claim 16 wherein step 4 comprises dialysis.

19. The process of claim 16 wherein the pharmaceutical agent is selected from:

therapeutic agent and diagnostic agent.

20. The process of claim 16 wherein the nanoparticulate dispersion is characterized by a Z-average particle diameter less than 400 nm as measured by photon correlation spectroscopy.

21. The process of claim 16 wherein the base is selected from any one or a combination of the following:

NaOH

KOH

CsOH trialkyl amines and pyridine.

22. The process of claim 16 wherein the neutralizing acid is selected from:

a weak acid and a strong acid.

23. The process of claim 16 wherein the neutralizing acid is selected from any one of the following:

HCl $HNO_3$ $HClO_4$ $H_2SO_4$ formic acid propionic acid acetic acid and butyric acid.

24. The process of claim 16 wherein the surface modifier is a mixture selected from the following:

an anionic surfactant a nonionic surfactant a polymeric molecule and an oligomeric molecule.

25. The process of claim 16 wherein the concentration of the dispersion is achieved by any one of the methods selected from the following:

diafiltration dialysis and evaporation.

26. The process of claim 16 wherein the nanoparticulate dispersion is characterized by a Z-average particle diameter less than 300 nm a measured by photon correlation spectroscopy.

27. The process of claim 16 wherein the pharmaceutical agent is an X-ray contrast agent.

28. The process of claim 16 wherein the nanoparticulate pharmaceutical agent is concentrated to contain anywhere between 2 to 20% of the agent.

29. The method of claim 16 practiced in any mode selected from the following:

a batch process, a semicontinuous batch process, and a continuous process.

30. The method of claim 16 wherein one of the surface modifers is base degradable.

* * * * *